United States Patent [19]

Zahm et al.

[11] Patent Number: 5,455,226
[45] Date of Patent: Oct. 3, 1995

[54] EGF-CONTAINING PHARMACEUTICAL COMPOSITION FOR THE TREATMENT OF BRONCHOPULMONARY PATHOLOGIES

[75] Inventors: Jean-Marie Zahm; Edith Puchelle; Denis Pierrot; Rachid Benali, all of Reims Cédex; Aline Moreau, Paris, all of France

[73] Assignees: Synthelabo, Le Plessis Robinson; Inserm, Paris, both of France

[21] Appl. No.: 983,725

[22] Filed: Dec. 1, 1992

[30] Foreign Application Priority Data

Dec. 2, 1991 [FR] France .................... 91 14886

[51] Int. Cl.⁶ .................... A61K 38/00; C07K 2/00; C07K 4/00
[52] U.S. Cl. .................... 514/12; 530/388.24
[58] Field of Search .................... 514/12; 530/388.24

[56] References Cited

U.S. PATENT DOCUMENTS 4,959,353  9/1990  Brown .................... 514/12

FOREIGN PATENT DOCUMENTS 0454026  10/1991  European Pat. Off. .
WO91/04728  4/1991  WIPO .

OTHER PUBLICATIONS

Dijke et al., *Biotech. Review*, vol. 7, 794–798, 1989.
Paulsen, *Scand. J. Gasteroenterol.*, vol. 128, 20–21, 1987.
American Journal of Respiratory Cell and Molecular Biology, vol. 4, No. 2, Feb. 1991, pp. 95–101.
Laboratory Investigations, vol. 59, No. 1, Jul. 1988, pp. 25–35.
Laboratory Investigations, vol. 63, No. 4, Oct. 1990, pp. 455–466.
Laboratory Investigations, vol. 60, pp. 539–547.
Am. J. Physiol., 1988, 255, C237–C245.
Am. Rev. Respir. Dis. 1985, 132, 311–320.

*Primary Examiner*—Jill Warden
*Assistant Examiner*—Lynn Touzeau
*Attorney, Agent, or Firm*—Jacobson, Price, Holman & Stern

[57] ABSTRACT

EGF (Epidermal Growth Factor)-containing pharmaceutical composition and method for the treatment of bronchopulmonary pathologies accompanied by lesions of the bronchial epithelium utilising EGF.

1 Claim, No Drawings

EGF-CONTAINING PHARMACEUTICAL COMPOSITION FOR THE TREATMENT OF BRONCHOPULMONARY PATHOLOGIES

BACKGROUND OF THE INVENTION

The EGF growth factor (Epidermal Growth Factor) is a polypeptide synthesised in numerous organs and whose stimulatory action on cell proliferation has been demonstrated on glial cells, mesenchymatous cells and epithelial cells in culture. In the respiratory epithelium, St George et al. (Am. J. Respir. Cell Mol. Biol., 1991, 4, 95–101) have shown that EGF is involved in the foetal development of the tracheobronchial secretory system of monkeys. Stahlman et al. (Lab. Invest., 1989, 60, 539–547) have demonstrated, by immunochemistry, the presence of EGF in respiratory tissue during foetal development in man. On the other hand, it has been shown in animals that EGF has no effect on the proliferation of epithelial cells of dog trachea in culture but that it promotes the response of these same cells to stimulation by beta-adrenergics (Van Scott, Am. J. Physiol., 1988, 255, C237–C245). In contrast, Wu et al. (Am. Rev. Respir. Dis., 1985, 132, 311–320) have reported that the omission of EGF from the culture medium induces a decrease in the proliferation of human nasal epithelial cells.

SUMMARY OF THE INVENTION

The Applicants have studied the effect of EGF on the growth, differentiation and functional activity of human respiratory cells in culture. Furthermore, using in vitro models of wounds of the respiratory epithelium, the Applicants have demonstrated a potential effect of EGF on the repair of these wounds.

Accordingly the present invention provides an EGF-containing pharmaceutical composition which is useful for the treatment of bronchopulmonary pathologies accompanied by wounds of the bronchial epithelium (accidental intoxications, bronchopulmonary infections, chronic bronchitides and emphysemas). The invention also provides a method for the treatment of bronchopulmonary pathologies accompanied by wounds of the bronchial epithelium in a patient suffering therefrom, which method comprises administering to said patient a therapeutically effective amount of Epidermal Growth factor.

DETAILED DESCRIPTION OF THE INVENTION

Cultures of respiratory epithelial cells are obtained from nasal polyps by the technique of explants (growth of cells around the explant) and by the technique of dissociated cells cultured in a three-dimensional collagen matrix (collagen lattice).

The explants are cultured in the presence of varying concentrations (0, 5, 10 and 20 ng/ml) of EGF (EGF from mouse submaxillary glands, ref. E 4127, Sigma). The growth area around the explants is quantified after 3 and 4 days of culture. The percentage of growth area covered with ciliated cells as well as the ciliary beat frequency were measured after 3 days of culture. For the collagen lattice culture technique, the number of cells in culture was quantified up to 11 days after of culture, and this in the absence and in the presence of EGF (10 ng/ml).

The results obtained show that increasing the concentration of EGF in the culture medium (up to 20 ng/ml) results in a substantial increase in the growth area ($p<0.05$) around the explants (the rate of cell proliferation is higher when the cells cultured in a collagen lattice are in contact with EGF at a concentration of 10 ng/ml, compared with cultures without EGF). After 8 days of culture, the number of cells is twice as high in the presence of EGF. When the respiratory epithelial cells are cultured in a collagen lattice, the presence of EGF in the culture medium promotes the formation of tubular type three-dimensional structures. This tubule-developing process has been described during bronchial glandular morphogenesis. In the absence of EGF, the epithelial cells tend to form a two-dimensional cellular layer.

In the case of the functional activity of ciliated cells, it is observed that a higher percentage (43%) of the growth surface is covered with ciliated cells in the presence of 20 ng/ml of EGF compared with the percentage obtained during culture in the absence of EGF (30%). The ciliary beat frequency is also substantially higher (14.5 Hz) in the presence of 20 ng/ml of EGF compared with the ciliary beat frequency measured in the absence of EGF (12.6 Hz).

The study of the repair of wounds of the respiratory epithelium was performed on an in vitro model. Thirty to 50 cells are detached from the culture by means of a micromanipulator so as to expose the collagen matrix on which the epithelial cells proliferate. The repair of this injured region is monitored as a function of time on cultures in the presence of EGF (10 ng/ml) or in the absence of EGF. For the technique of culture of dissociated cells in a collagen lattice, the effect of EGF on the retraction of the collagen lattice was studied after 8 days of culture. This retraction is quantified by measuring the area of the collagen lattice.

In the presence of an EGF concentration of 10 ng/ml, the wounds are repaired more rapidly than in the absence of EGF (with EGF, the slope of the regression line $=-71.8$; without EGF, the slope of the regression line $=-42.3$).

In the case of the retraction of the collagen lattices by the superficial respiratory epithelial cells, it is observed that after 8 days of culture in the presence of EGF, the lattice area is substantially smaller (660 $mm^2$) than the area obtained without EGF (800 $mm^2$). It is accepted that this process of retraction of a collagen lattice by cultured cells is representative of the wound repair phenomena of in vivo (Ehrlich, Tissue and Cell, 1990). This retraction by respiratory cells had never been demonstrated up until now.

The applicants also studied the dose-dependent effect of EGF on the wound repair with a quantification of the extent of the stimulation relative to a control, as well as comparative data between the EGF obtained from mouse submaxillary glands and recombinant human EGF (Sigma, Ref. E-3264).

In vitro model of lesion of the respiratory epithelium:

Surface epithelial cells dissociated from nasal polyp are cultured on a collagen I matrix in RPMI culture medium supplemented with hydrocortisone, retinoic acid, insulin and EGF (epidermal growth factor). After about 3 days of culture, when the cells have become confluent, the supplemented culture medium is replaced with unsupplemented RPMI medium. After incubating for 12 hours in the presence of unsupplemented medium, the culture is placed on the stage of an inverted microscope equipped with a micromanipulator. A microcapillary, guided by the micromanipulator, makes it possible to detach cells, thus creating a wound with a surface area of about 100,000 $\mu m^2$. The unsupplemented culture medium is then replaced with culture medium containing only EGF at different concentrations. Video recordings of the injured culture are then made every hour. Using these video recordings, an image analyser makes it possible to monitor the variation of the surface area of the wound as a function of time. A regression line between the surface area of the wound (expressed in $\mu m^2$) and the time (expressed in hours) makes it possible to calculate the slope of the regression line obtained, a slope which corresponds to the decrease in the surface area of the wound per unit of time. The latter parameter corresponds to the repair index (the higher the index, the faster the repair).

EGF dose-dependent effect:

Eight nasal polyps were used to culture respiratory epithelial cells (5 culture dishes per polyp). In each of these dishes, the injured cultures are incubated either in the presence of unsupplemented culture medium, or in the presence of culture medium supplemented with EGF at various concentrations (5, 10, 20 or 50 ng/ml). From the variation of the surface area as a function of time (the repair index corresponds to the slope of the regression line between the surface area of the wound and time), we calculated the repair index. This index is then expressed relative to the repair index obtained with the EGF-free culture medium used as control. The results obtained show a systematic increase in the repair index for wounds in the presence of EGF. At a concentration of 5 and 10 ng/ml, EGF stimulates the repair by 38% and 36% respectively. At the concentration of 20 ng/ml, the stimulation is 49%. At a concentration of 50 ng/ml of EGF, the repair index is significantly ($p<0.05$) reduced compared with the index obtained with 20 ng/ml of EGF.

In conclusion, EGF stimulates in vitro the repair of respiratory epithelial wound. This stimulation is maximum at the concentration of 20 ng/ml and it is lower for concentrations above 20 ng/ml.

Comparison of the EGF of mouse submaxillary gland and recombinant human EGF:

This study was carried out under the same experimental conditions as above. The repair index for the wounds was quantified in the presence of unsupplemented culture medium and in the presence of culture medium supplemented either with EGF of mouse submaxillary gland (m-EGF: 10 ng/ml), or with recombinant human EGF (h-EGF: 10 ng/ml).

There is no significant difference between the repair index obtained with m-EGF (11215 $\mu m^2/h$) and the repair index obtained with h-EGF (11492 $\mu m^2/h$), both being significantly higher than the repair index obtained without EGF (6235 $\mu m^2$).

In conclusion, EGF obtained from mouse submaxillary glands and recombinant human EGF have the same effect on the repair of wounds of the respiratory epithelium.

EGF promotes the repair of wounds of the respiratory epithelium according to an effect which is dose-dependent. The maximum effect is obtained at a concentration of 20 ng/ml of EGF, with a stimulation of nearly 50% of the repair index compared with a control without EGF.

The comparative study of the EGF of mouse submaxillary glands and recombinant human EGF does not show a significant difference between the effect of these two forms of EGF.

EGF stimulates the growth and differentiation of human respiratory epithelial cells, and this according to a dose-dependent effect: increase in cell proliferation and in the functional activity of ciliated cells.

EGF promotes the cicatrisation of wounds of the respiratory epithelium.

EGF promotes the development of the tubules observed during bronchial glandular morphogenesis.

EGF stimulates ciliary activity in vitro.

EGF can therefore promote the repair of the bronchial epithelium following any damage to it by a toxic substance, an infection, an oxidant and the like.

The EGF-containing pharmaceutical compositions of the invention can be administered intravenously or by inhalation and are provided in the form of solutions, solutions for nebulisation, sprays and the like.

We claim:

1. A method for treating ciliated respiratory epithelial wounds in a patient suffering therefrom, which method comprises promoting healing of said wounds by administering to said patient a therapeutically effective amount of Epidermal Growth Factor in combination with a physiologically acceptable carrier at a concentration of 5 to 20 ng/ml.

* * * * *